United States Patent
Curry

(10) Patent No.: US 8,021,369 B2
(45) Date of Patent: Sep. 20, 2011

(54) NAVIGATED FEMORAL NECK RESECTION GUIDE AND METHOD

(75) Inventor: Alexander Curry, Saddle Brook, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 903 days.

(21) Appl. No.: 11/451,101

(22) Filed: Jun. 12, 2006

(65) Prior Publication Data

US 2007/0299452 A1    Dec. 27, 2007

(51) Int. Cl.
*A61B 17/58* (2006.01)
*A61B 17/60* (2006.01)
*A61F 2/00* (2006.01)

(52) U.S. Cl. .......................................... 606/88
(58) Field of Classification Search ............ 606/88, 606/89, 79, 86 R, 87, 104, 82; 623/22.11, 623/23.15
See application file for complete search history.

(56) References Cited

U.S. PATENT DOCUMENTS

| | | | |
|---|---|---|---|
| 4,388,921 A * | 6/1983 | Sutter et al. ............ 606/71 |
| 4,421,112 A | 12/1983 | Mains et al. |
| 4,484,570 A * | 11/1984 | Sutter et al. ............ 606/282 |
| 4,718,413 A | 1/1988 | Johnson |
| 4,892,093 A | 1/1990 | Zarnowski et al. |
| 4,926,847 A | 5/1990 | Luckman |
| 4,959,066 A | 9/1990 | Dunn et al. |
| 5,007,935 A | 4/1991 | Vincent et al. |
| 5,269,784 A * | 12/1993 | Mast ............................. 606/288 |
| 5,275,603 A | 1/1994 | Ferrante et al. |
| 5,312,411 A * | 5/1994 | Steele et al. ................... 606/88 |
| 5,352,229 A * | 10/1994 | Goble et al. .................... 606/75 |
| 5,405,349 A | 4/1995 | Burkinshaw et al. |
| 5,411,505 A | 5/1995 | Mumme |
| 5,462,550 A * | 10/1995 | Dietz et al. ................ 606/86 R |
| 5,514,139 A | 5/1996 | Goldstein et al. |
| D375,791 S * | 11/1996 | Goble et al. ................ D24/145 |
| 5,578,034 A * | 11/1996 | Estes ............................ 606/281 |
| 5,578,037 A * | 11/1996 | Sanders et al. ................. 606/80 |
| 5,597,379 A | 1/1997 | Haines et al. |
| 5,607,431 A | 3/1997 | Dudasik et al. |
| 5,616,147 A * | 4/1997 | Gadelius ...................... 606/102 |
| 5,662,656 A | 9/1997 | White |
| 5,688,280 A | 11/1997 | Booth, Jr. et al. |
| 5,690,632 A * | 11/1997 | Schwartz et al. ............ 606/302 |
| 5,735,856 A | 4/1998 | McCue et al. |
| 5,746,771 A | 5/1998 | Clement, Jr. et al. |
| 5,810,823 A * | 9/1998 | Klaue et al. .................. 606/289 |
| 5,810,829 A | 9/1998 | Elliott et al. |
| 5,897,559 A | 4/1999 | Masini |

(Continued)

FOREIGN PATENT DOCUMENTS

FR       2790198       9/2000
(Continued)

*Primary Examiner* — Thomas C Barrett
*Assistant Examiner* — David W Bates
(74) *Attorney, Agent, or Firm* — Lerner, David, Littenberg, Krumholz & Mentlik, LLP

(57) ABSTRACT

A femoral neck resection guide assembly for use in minimally invasive hip surgery is disclosed. The assembly includes a guide portion having at least two spaced resection guide surfaces for guiding a cutting tool. A bushing and fastener elements are also included in the assembly for cooperating with and fixing the guide portion to the bone. Preferably, the assembly allows for initial connection of the guide portion to the bone and polyaxial rotation of the guide before such is statically affixed.

32 Claims, 15 Drawing Sheets

U.S. PATENT DOCUMENTS

| | | | |
|---|---|---|---|
| 5,925,049 A | 7/1999 | Gustilo et al. | |
| 5,954,722 A * | 9/1999 | Bono | 606/281 |
| 5,961,520 A * | 10/1999 | Beck et al. | 606/232 |
| 6,110,211 A | 8/2000 | Weiss | |
| 6,120,510 A | 9/2000 | Albrektsson et al. | |
| 6,126,663 A * | 10/2000 | Hair | 606/324 |
| 6,231,606 B1 * | 5/2001 | Graf et al. | 606/232 |
| 6,503,255 B1 | 1/2003 | Albrektsson et al. | |
| 6,575,975 B2 * | 6/2003 | Brace et al. | 606/86 B |
| 6,613,053 B1 * | 9/2003 | Collins et al. | 606/293 |
| 6,676,706 B1 | 1/2004 | Mears et al. | |
| 6,716,214 B1 | 4/2004 | Jackson | |
| 6,964,664 B2 * | 11/2005 | Freid et al. | 606/281 |
| 7,458,977 B2 * | 12/2008 | McGinley et al. | 606/130 |
| 7,488,325 B2 * | 2/2009 | Qian | 606/96 |
| 2002/0065562 A1 | 5/2002 | Storer et al. | |
| 2003/0187514 A1 | 10/2003 | McMinn | |
| 2004/0153083 A1 | 8/2004 | Nemec et al. | |
| 2004/0236341 A1 * | 11/2004 | Petersen | 606/89 |
| 2005/0038444 A1 * | 2/2005 | Binder et al. | 606/96 |
| 2005/0080424 A1 | 4/2005 | Cuckler et al. | |
| 2005/0245934 A1 * | 11/2005 | Tuke et al. | 606/79 |
| 2006/0025775 A1 * | 2/2006 | Malkani | 606/89 |
| 2006/0217713 A1 * | 9/2006 | Serhan et al. | 606/61 |
| 2006/0271058 A1 * | 11/2006 | Ashton et al. | 606/96 |

FOREIGN PATENT DOCUMENTS

| | | |
|---|---|---|
| RU | 2305515 C1 * | 6/2006 |
| WO | WO-8803781 | 6/1988 |
| WO | 02/26145 | 4/2002 |
| WO | WO 0226145 A1 * | 4/2002 |

\* cited by examiner

NAVIGATED FEMORAL NECK RESECTION GUIDE AND METHOD

FIELD OF THE INVENTION

The present invention relates to orthopedic cutting blocks for use in resecting the neck of a femur, and more particularly, to a femoral neck resection guide for resecting at least a portion of the neck of a femur and facilitating the removal of the same.

BACKGROUND OF THE INVENTION

At the present time, there is a great emphasis toward minimally invasive techniques in joint replacement surgeries. For example, minimally invasive hip replacements, including two-incision hip arthroplasty and single anterior approach arthroplasty, are currently the preferred methods of performing surgery of this type. While there are benefits to performing these minimally invasive techniques (i.e.—quicker recovery time, less scarring, etc. . . . ), there are also requirements and difficulties associated with the methods.

One of the primary objectives during a minimally invasive hip surgical technique is to remove the femoral head and neck portions without dislocating the femoral head from the acetabulum. By not dislocating the femoral head, the hip capsule may be preserved, thereby maintaining stability and power of the hip joint. This is typically accomplished by performing the femoral neck osteotomy and the resection of the femoral head in situ. Unfortunately, there is significant difficulty in performing these resections in situ. The small size of the incisions used in minimally invasive surgery and the lack of instruments directed to performing the bone cuts in such a small space provide significant hurdles for a surgeon.

Heretofore, at least one femoral neck resection guide has been proposed. Commonly owned United States Patent Publication No. 2006/0025775 (the '775 publication), the disclosure of which is hereby incorporated by reference herein, teaches a femoral neck resection guide suitable to aid in the aforementioned femoral neck osteotomy. However, such resection guide does not necessarily provide significant adaptability to the varying landscape defined by the differing geometry of the femoral neck.

For the foregoing reasons, there exists a need for a femoral neck resection guide for and method of performing minimally invasive hip resection and bone removal, where a guide is provided that is capable of being manipulated in situ to provide for very accurate cuts to the proximal portion of the femur during hip surgery.

SUMMARY OF THE INVENTION

A first aspect of the present invention is a femoral neck resection guide comprising at least two spaced resection guide surfaces for guiding a cutting tool, the guide surfaces being spaced apart a distance sufficient to allow resection of at least a portion of the femoral neck, and means for attaching the guide surfaces to a portion of the neck of the femur.

Another embodiment of the present invention is a femoral neck resection guide comprising a generally H-shaped body having a top surface and a bottom surface. The body includes two cutting surfaces arranged on opposing sides of the body, the cutting surfaces adapted to make two cuts on a neck section of the femur, at least one aperture for receiving at least one bone connection device to connect the body to the neck section of the femur, and a coupling element adjacent the aperture for engaging an extraction tool while the connection device is engaged to the femoral neck.

Another embodiment of the present invention is a femoral neck resection guide comprising a body. The body has at least two spaced resection guide surfaces for guiding a cutting tool, means for attaching the body and the at least two spaced resection guide surfaces to a portion of the neck of the femur, and a combination insertion and extraction tool formed integral with the body.

Another aspect of the present invention is a femoral neck resection instrument system or kit comprising a cutting guide having two spaced resection guide surfaces for guiding a bone resection tool. The cutting guide according to this embodiment includes a bone connection device for connecting the cutting guide to a femoral neck and a tool coupling element. The system or kit also includes an alignment instrument releasably engageable with the cutting guide for aligning the resection guide surfaces and a removal instrument for releasably engaging the tool coupling element of the cutting guide while the bone connection device is connected to the femoral neck.

Another aspect of the present invention is a femoral neck resection guide kit. The kit comprises at least two different sized femoral neck resection guides. Each of the guides includes at least two spaced resection guide surfaces for guiding a cutting tool and means for attaching the guide surfaces to a portion of the neck of the femur. The guide surfaces are spaced apart a distance sufficient to allow resection of substantially all of the femoral neck.

Another aspect of the present invention is a method of removing a neck of a femur comprising providing a femoral neck resection guide having at least two cutting surfaces, aligning the femoral neck resection guide with respect to a femoral neck, connecting the femoral neck resection guide to at least a portion of the neck of the femur, making at least two cuts defining a resection portion, the cuts corresponding to the at least two cutting surfaces of the femoral neck resection guide, and removing the femoral neck resection guide.

Still another aspect of the present invention is a femoral neck resection guide assembly including a body portion, at least two spaced resection guide surfaces for guiding a cutting tool, a bushing and a fastener element. The body portion preferably further includes a body aperture formed therethrough, the guide surfaces are preferably capable of being connected to the body portion, the bushing is preferably capable of being inserted in the body aperture and the fastener element is preferably capable of being disposed through the bushing aperture. The guide surfaces are also preferably spaced apart a distance sufficient to allow resection of at least a portion of the femoral neck, and may or may not include slots, with or without closed ends. In addition, the cooperation between the bushing and the bushing aperture may allow for polyaxial rotation of the body portion with respect to the bushing. In such a case, full insert of the fastener element through the bushing aperture preferably prevents such rotation. In order to prevent rotation of the bushing with respect to a bone surface, the bushing may include a plurality of spikes for engagement with the bone.

Yet another aspect of the present invention is a method of removing a neck of a femur. Such method may include the steps of providing a femoral neck resection guide assembly including a guide, a bushing and a fastener element, aligning at least the guide and bushing with respect to the femoral neck, connecting the bushing with a surface of the femoral neck, positioning the guide with respect to the bushing, locking the guide with respect to the bushing and the femoral neck by utilizing the fastener element, and resecting at least a portion of the femoral neck with a cutting tool guided by the guide. The method may further include the step of removing the femoral neck resection guide assembly, where such removal also includes removing a resected portion of the femoral neck. A navigation tracker may be utilized to properly position and monitor the guide. The positioning step may include polyaxially rotating the guide with respect to the bushing, subsequent to the bushing being attached to a portion of the femoral neck. The fastener element may be a screw or other suitable fastener.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

In describing the preferred embodiments of the subject matter illustrated and to be described with respect to the drawings, specific terminology will be resorted to for the sake of clarity. However, the invention is not intended to be limited to the specific term and includes all technical equivalence which operates in a similar manner to accomplish a similar purpose.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
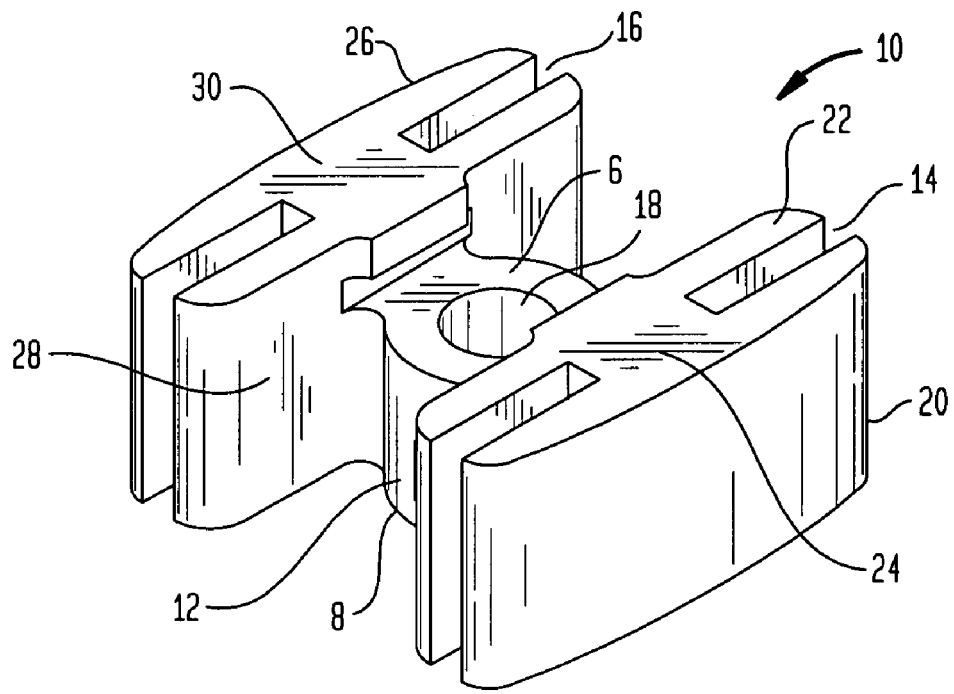
FIG. 1 is a top perspective view of the femoral neck resection guide according to an embodiment of the present invention.
Figure 2:
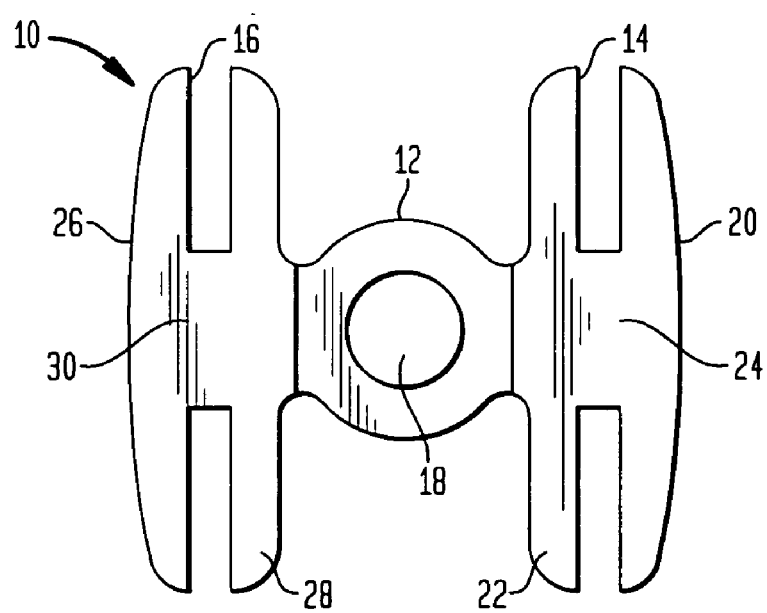
FIG. 2 is a bottom plan view of the femoral neck resection guide according to FIG. 1.
Figure 3:
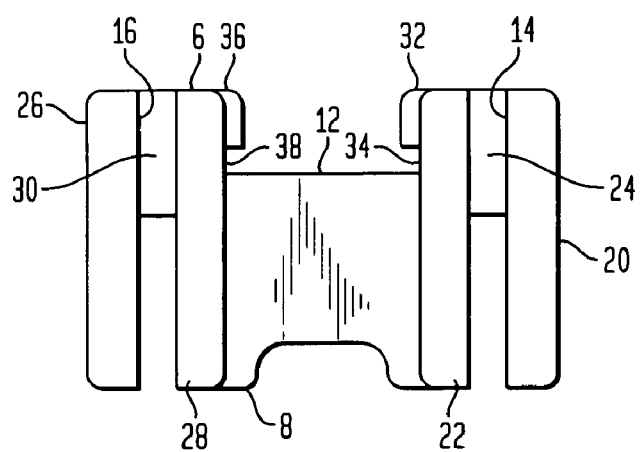
FIG. 3 is a front plan view of the femoral neck resection guide according to FIG. 1.
Figure 4:
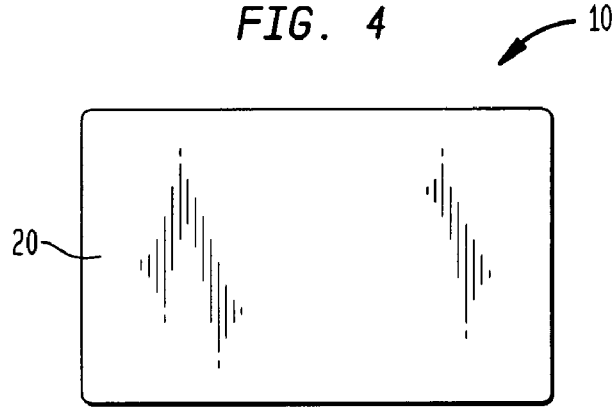
FIG. 4 is right side plan view of the femoral neck resection guide according to FIG. 1.

Referring to the drawings, wherein like reference numerals represent like elements, there is shown in the Figures, in accordance with embodiments of the present invention, a femoral neck resection guide designated generally by reference numeral 10. In a preferred embodiment, as shown in FIGS. 1-4, resection guide 10 is designed to be used in resecting the femoral neck. However, it is contemplated that other embodiments of the present invention can be designed to be used in resecting other bones in other areas of the body. As shown in FIG. 1, resection guide 10 is of unitary construction having a top surface 6 and a bottom surface 8. Resection guide 10 is adapted for attaching to a neck portion 2 of a femur 1, with bottom surface 8 contacting the bone surface. In a preferred embodiment, resection guide 10 includes a body 12, first cutting slot 14, second cutting slot 16, and aperture 18 for facilitating connection to the aforementioned neck portion 2 of femur 1. It should be noted that in preferred embodiments, slots 14 and 16 are spaced so that substantially all of the femoral neck may be resected. However, it is contemplated that slots 14 and 16 can be spaced any distance capable to provide a desired resected portion.

As shown in FIGS. 1-4, body 12 is of a generally cylindrical shape with aperture 18 extending through its center and cutting slots 14 and 16 attached on either side. It is contemplated that body 12 can be of any shape or size, can be configured so as to include any number of apertures 18 at any location and can be attached to any number of cutting surfaces in any manner suitable for facilitating the cutting of a bone. For example, body 12 can be square shaped and include aperture 18 at any portion thereon and cutting surfaces 14 and 16 formed along any side of the square. A rounded shape helps prevent soft tissue damage from occurring during insertion and removal.

As shown in FIGS. 1-4, slots 14 and 16 define cutting surfaces for guiding a cutting instrument. These slots are substantially identical and are attached to body 12 on opposing sides. However, it is contemplated that cutting slots 14 and 16 can be of different configurations and can be attached to body 12 in any manner necessary to facilitate the cutting of a particular bone. In the preferred embodiment shown in the Figures, cutting slots 14 and 16 are formed integral with body 12. However, it is contemplated that pieces including cutting slots 14 and 16 can be formed separately and thereafter permanently or detachably connected to body 12. In the case where the pieces are detachably connected, resection guide 10 is of a modular design, allowing for assembly prior to being inserted into the body or in situ. Assembling in situ can be useful in inserting pieces of resection guide 10 through very small incisions.

In the preferred embodiment, first cutting slot 14 is formed by first exterior wall 20, first interior wall 22, and connected by first bridge 24. Second cutting slot 16 is formed by second exterior wall 26, second interior wall 28, and connected by second bridge 30. First exterior wall 20 and first interior wall 22 are connected together by first bridge 24. Bridge 24 is narrower and shorter in height (from the top surface 6 towards the bottom surface 8) than first exterior wall 20 and first interior wall 22, which are substantially the same in dimension and shape. Essentially, bridge 24 extends between first exterior wall 20 and first interior wall 22, to create the slot defined by the two walls. Bridge 24 only extends partially on the depth of slot 14 from top surface 6 towards bottom surface 8 (best shown in FIG. 3) and only extends partially along the depth of first exterior wall 20 and first interior wall 22 (best shown in FIG. 2). At the connection of first cutting slot 14 and body 12, a ledge 32 is formed. This ledge 32 hangs over body 12 to form a groove 34 for aiding in the connection with other tools. This will be discussed further below. In a substantially similar fashion, second exterior wall 26 and second interior wall 28 are connected together by second bridge 30, and second cutting slot 16 forms a ledge 36 and groove 38. Since the bottom of slots 14 and 16 are left open, this allows greater travel of the saw blade along the guide slot.

Figure 5:
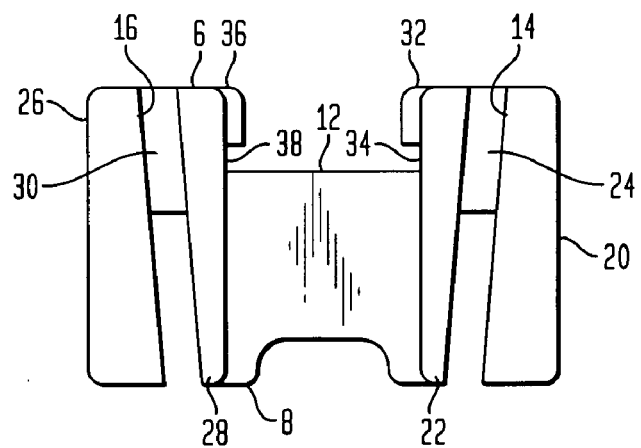
FIG. 5 is a front plan view of the femoral neck resection guide according to another embodiment of the present invention.

As shown in FIG. 5, cutting slots 14 and 16 may be non-parallel or angled inwardly from top surface 6 to bottom surface 8, at an angle A. This angle allows for cuts to made at a corresponding angle, thereby creating a cut section of bone that is likewise angled inwardly from a top surface to a bottom surface. Such a configuration is desirable for facilitating the easy removal of both the guide and the cut section of bone from the body of a patient. In certain embodiments, angle A is approximately five degrees. However, it is contemplated that angle A can be any amount for creating a desired cut section of bone.

Figure 6:
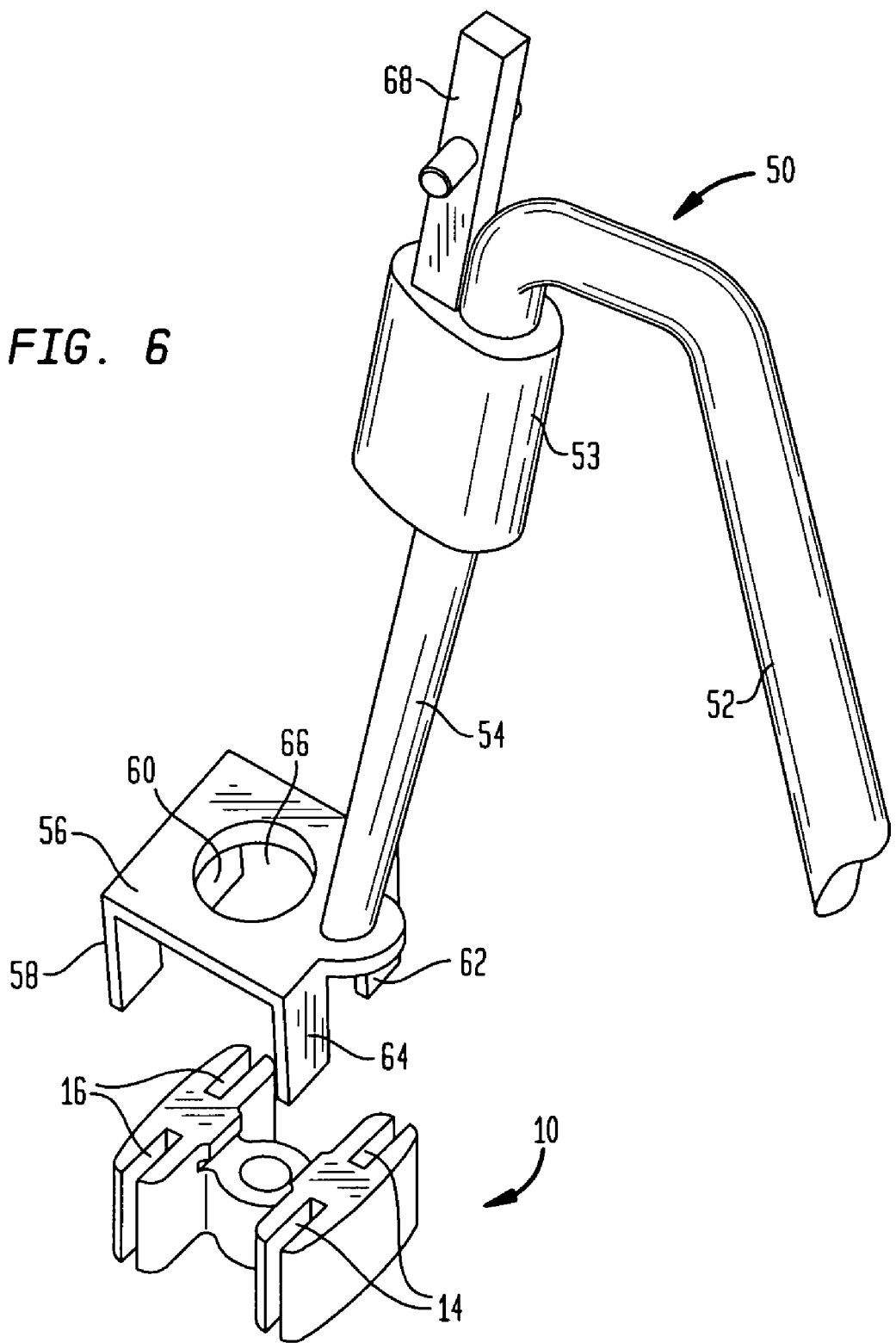
FIG. 6 is a top perspective view of the femoral neck resection guide according to FIG. 1 with an alignment guide adjacent thereto.
Figure 7:
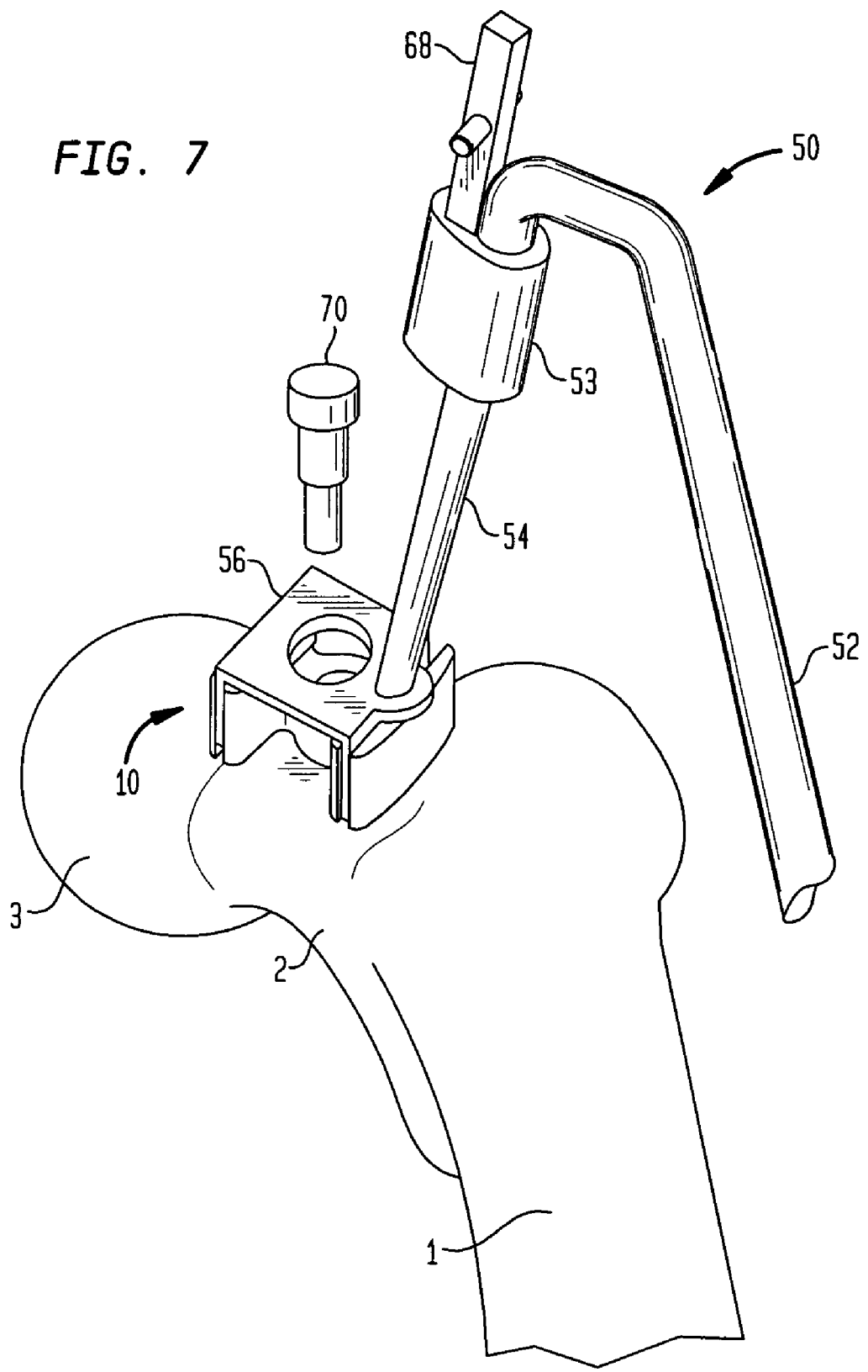
FIG. 7 is a top perspective view of the femoral neck resection guide according to FIG. 1 placed adjacent the neck of the femur, with an alignment guide attached thereto and a screw adjacent thereto.

FIGS. 6 and 7 illustrate an alignment guide, generally denoted as 50, and its cooperation with resection guide 10. As shown in FIGS. 6 and 7, alignment guide 50 includes elongate guide portion 52 having one end coupled to a coupler 53. A shaft 54 extends from coupler 53 and includes a platform 56 having four fingers 58, 60, 62, and 64, and central opening 66. Furthermore, alignment guide 50 may optionally include navigation tracker mount 68 for utilizing computer or other navigation tracking systems. The use of such a tracker is shown in U.S. Pat. Nos. 6,021,343 and 6,434,415, the disclosures of which are hereby incorporated by reference herein. Elongate guide portion 52 acts as a handle to easily manipulate alignment guide 50. Coupler 53 provides a connection point for both shaft 54 and navigation tracker mount 68. Since shaft 54 connects with platform 56 manipulation of elongate portion 52 will, in turn, manipulate platform 56. Fingers 58, 60, 62, and 64 extend from platform 56 and are adapted to mate with slots 14 and 16 of resection guide 10. Opening 66 is essentially a hole through platform 56, allowing for access to body 12 of resection guide 10, when alignment guide 50 is engaged with resection guide 10.

In operation, as shown in FIG. 7, fingers 58, 60, 62, and 64 of alignment guide 50 are received within cutting slots 16 and 14 of resection guide 10. Fingers 58 and 60 extend into cutting slot 16 on either side of second bridge 30, while fingers 62 and 64 extend into cutting slot 14 on either side of first bridge 24. The fit between the finger and the slots is such that, absent a force, resection guide 10 remains engaged with alignment guide 50. However, it is contemplated that other coupling methods can be employed for connecting alignment guide 50 to resection guide 10 such as spring loaded quick releases or ball detents. Nevertheless, these mating relationships between resection guide 10 and alignment guide 50 allow for a surgeon to direct resection guide 10 through small incisions and into contact with a bone surface, such as neck portion 2 of femur 1, as shown in FIG. 7. If the resection guide 10 is modular and assembled in situ, guide 50 can engage slots 14 and 16 after being inserted through the incision.

Figure 8:
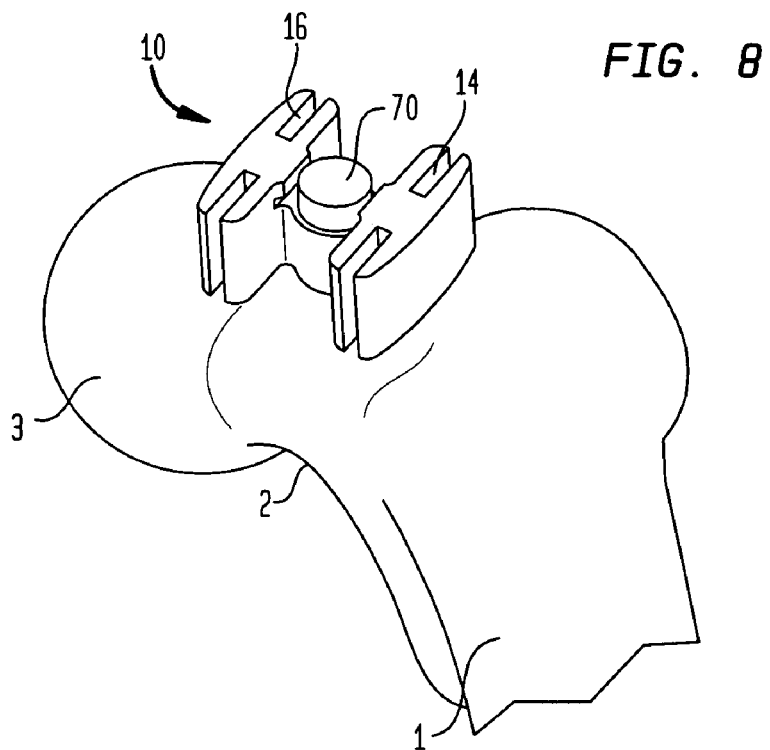
FIG. 8 is a top perspective view of the femoral neck resection guide according to FIG. 1 attached to the neck of the femur.

In an embodiment of the present invention, guide 10 is aligned so that slot 14 is positioned to allow for a cut which matches the angle of the femoral component as it would rest on the calcar (shown in FIGS. 7 and 8). This would allow a surgeon to simply utilize slot 14 to create the final cut for which the subsequently inserted femoral component would rest against. In other embodiments, guide 10 is aligned so that at least a portion of neck portion 2 of femur 1 can be resected. It is contemplated that the portion which is resected can be any size and can be oriented in any manner which allows for at least a portion of the femoral neck 2 to be removed. In other words, guide 10 can be aligned so that slots 14 and 16 allow for cuts to be made at any angle with respect to femur 1, as long as a portion of the neck is removed. Any removal of a portion of neck 2 necessarily detaches femoral head 3 from femur 1, thereby allowing for removal of head 3. If one of the cuts does not match the angle of the femoral component as it would rest against the calcar, at least one subsequent cut would need to be made to match the angle. It is contemplated that guide 10 can be aligned by various means. For example, alignment guide 50 may be configured so that shaft 52 may be aligned with the axis of femur 1. In this embodiment, aligning shaft 52 with the axis of femur 1 would automatically align guide 10 in a correct orientation. Similarly, as mentioned above, a navigation tracker may be utilized in order to properly align resection guide 10.

As is shown in FIG. 7, a screw 70 is provided for connecting resection guide 10 with a bone surface. Screw 70 has a head and a threaded portion and may be a standard bone screw known to one of ordinary skill in the art. It is contemplated the other means for attaching resection guide 10 to the bone. For example, a surgeon can utilize pins, nails, adhesive, among others, to attach resection guide 10 to a bone surface. Furthermore, it is also contemplated to utilize more than one attachment means for connecting resection guide 10 to a bone. For example, in another embodiment, resection guide 10 can be connected to a bone surface by two or more screws or two or more bone pins.

In operation, as best shown in FIG. 7, screw 70 is inserted through opening 66 of alignment guide 50 and into aperture 18 of resection guide 10. Screw 70 is then screwed into the bone using a typical tool such as a screw driver or drill until the head resets on the top surface of body 12. However, it is contemplated that prior to inserting screw 70 into aperture 18, opening 66 and aperture 18 can guide a drill or other hole forming tool to pre-form a hole. Thereafter, screw 70 can more easily be screwed into the bone. In a preferred embodiment, shown in FIG. 6, screw 70 is a self-tapping screw capable of creating a hole absent a drill or other hole making tool. Once the head of screw 70 is in engagement with resection guide 10, and in the preferred embodiment shown in the Figures, neck portion 2 of femur 1, alignment guide 50 can be removed from resection guide 10. This accomplished by disengaging fingers 58, 60, 62, and 64 from slots 14 and 16.

Figure 9:
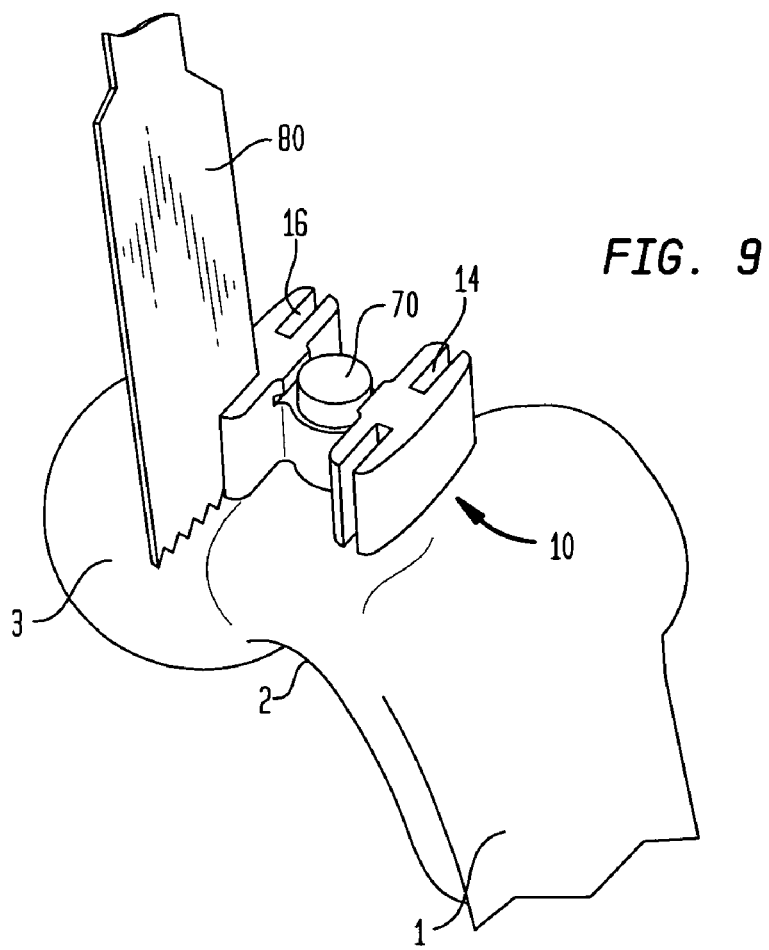
FIG. 9 is a top perspective view of the femoral neck resection guide according to FIG. 1 attached to the neck of the femur with a saw blade engaged therein.
Figure 10:
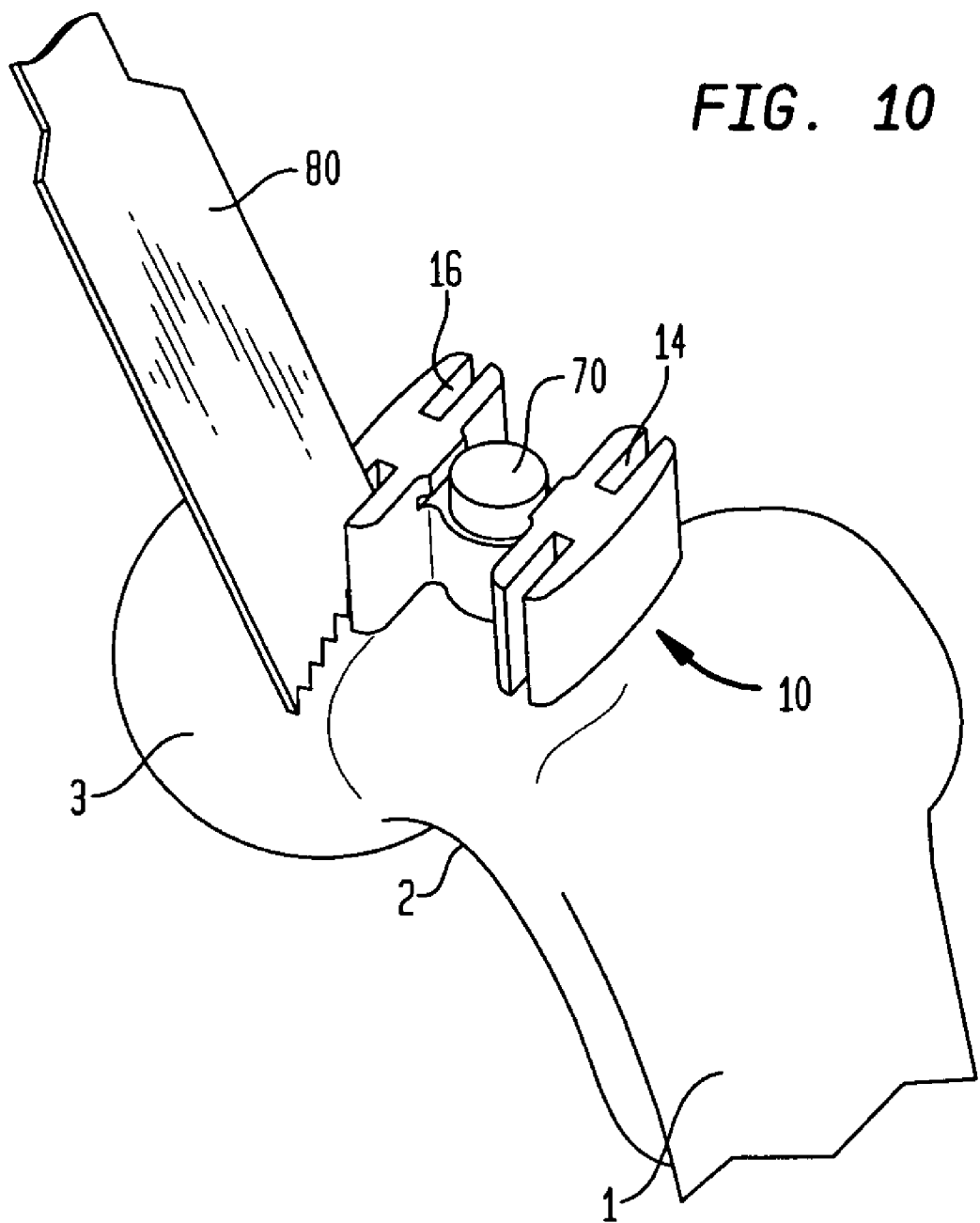
FIG. 10 is a top perspective view of the femoral neck resection guide according to FIG. 1 attached to the neck of the femur with a saw blade engaged therein in an angled fashion.

Upon removal of alignment guide 50, as shown in FIG. 8, resection guide 10 is attached to neck portion 2 of femur 1, in a position ready for a cutting operation. As shown in the figure, cutting slots 14 and 16 are aligned over the proximal and distal ends of neck portion 2. This allows for a resected neck portion 4, created using resection guide 10, to consist of the majority of neck portion 2. While use of guide 10 with respect to the femur is described, resection guide 10 can be aligned to cut any section of bone, in any part of the body. During the cutting process, a saw blade 80 is inserted into each slot 14 and 16, and the slot is used to guide saw blade 80 along and through the bone, as shown in FIG. 9. In operation, the surgeon inserts saw blade 80 into one slot and into contact with bone. The surgeon then moves the blade to cut and separate a cut portion 4 from the remainder of the bone. This includes angling saw blade 80 to navigate the saw around bridges 24 and 30, as shown in FIG. 10. It is contemplated that any suitable type of cutting tool can be utilized to perform these steps. For example, resection guide 10 can be used in conjunction with a milling device.

Figure 11:
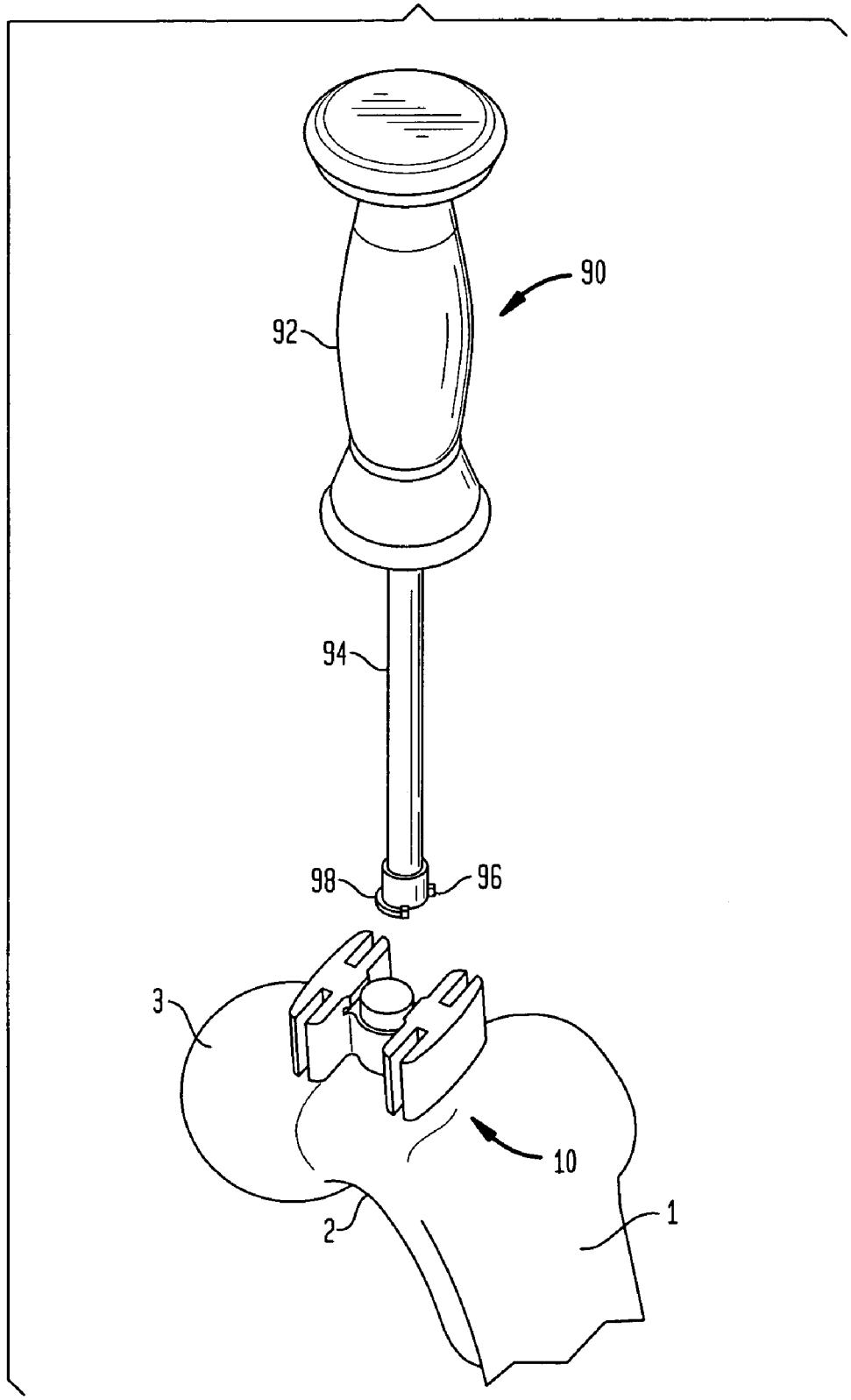
FIG. 11 is a top perspective view of the femoral neck resection guide according to FIG. 1 with an extraction tool adjacent thereto.
Figure 12A:
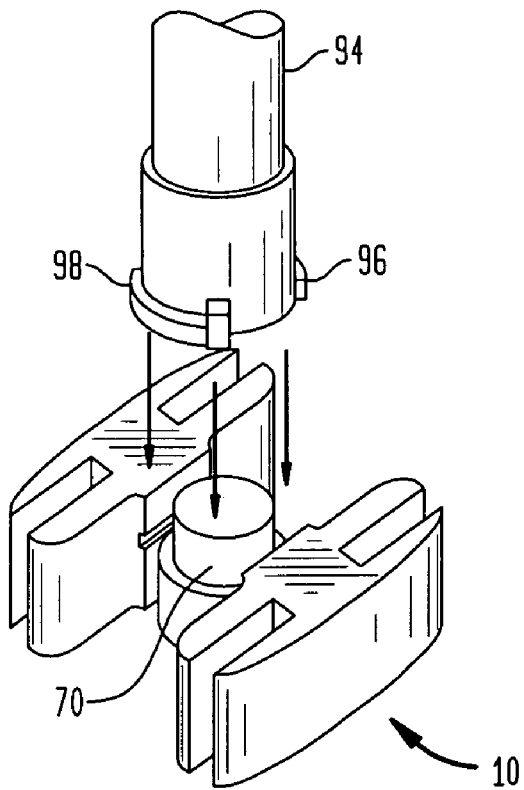
FIGS. 12a-12c shows a sequence of attaching an extraction tool of FIG. 11 to the femoral neck resection guide.
Figure 12B:
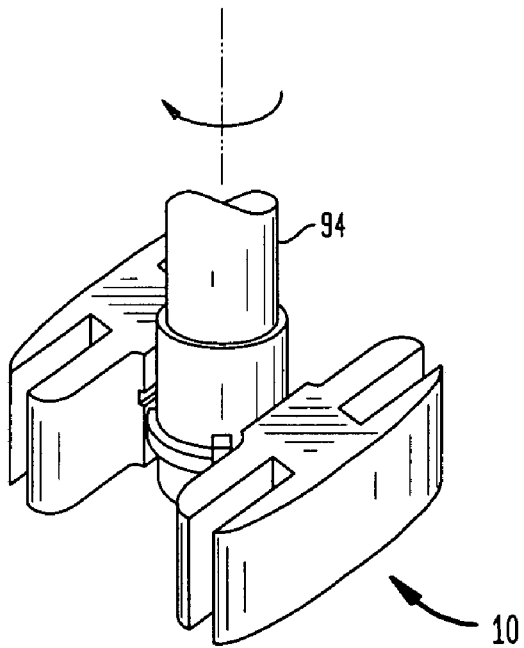
Figure 12C:
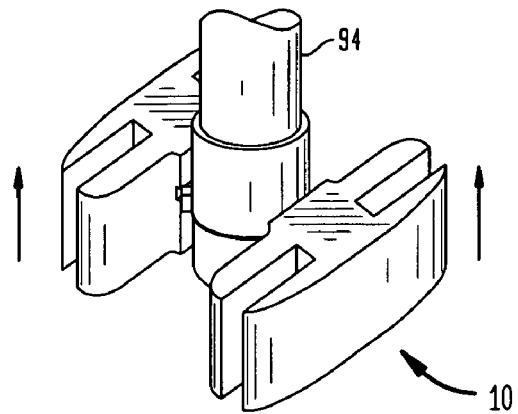

FIG. 11 depicts an extraction tool, generally denoted as 90. This tool includes a handle 92, at one end thereof, a shaft 94, and a coupling 96, at the other end thereof. Handle 92 is dimensioned for grasping by a surgeon. In the preferred embodiment, shaft 94 is generally cylindrical and connects handle 92 to coupling 96. Coupling 96 is configured so as to cooperate and preferably rotatably connect with resection guide 10. In a preferred embodiment, as shown in FIGS. 10-12, coupling 96 is configured for insertion into grooves 34 and 38 of resection guide 10. Coupling 96 is substantially cylindrical and includes two radially extending male portions 98 for reception under ledges 32 and 36 in grooves 34 and 38 on resection guide 10. Initially, coupling 96 is brought adjacent to body 12 without male portions 98 being in contact with grooves 34 and 38, however upon a clockwise turning of handle 90, and thus coupling 96, male portions 98 become disposed under ledges 32 and 36 and engage grooves 34 and 38 portions. This results in extraction tool 90 being fixably attached to resection guide 10. At this point, any movement applied to extraction tool 90 also moves resection guide 10. This is best shown in the sequence depicted in FIGS. 12*a*-12*c*. It is contemplated that extraction tool 90 can be configured and dimensioned in different ways. Similarly, coupling 96 can cooperate with resection guide 10 in many different fashions. For example, in other embodiments, coupling 96 can snap into a corresponding portion of resection guide 10 or screw into a threaded portion of resection guide 10.

Figure 13:
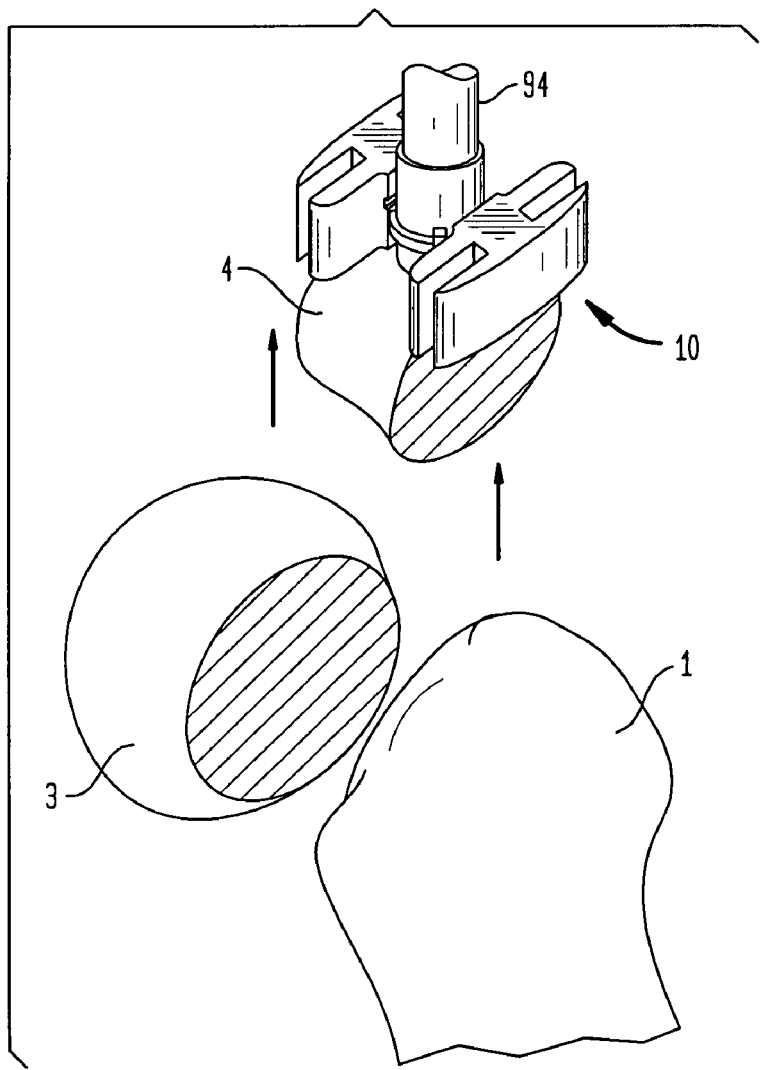
FIG. 13 is a top perspective view of the femoral neck resection guide being removed by the extraction tool along with a portion of the femoral neck subsequent to the cutting of the femoral neck.

The removal of the created resected portion 4 of neck portion 2 of femur 1 is shown in FIG. 13. With the aforementioned extraction tool 90 connected to resection guide 10, the surgeon, subsequent to the cuts being completed on the bone, removes resection guide 10 while it is connected to resected portion 4 by screw 70. Typically, resected portion 4 will be small enough to fit through the incision created in the tissue of a patient in order to insert resection guide 10. Furthermore, it should be noted that the exterior walls 20 and 26 of slots 14 and 16 may be curved to minimize the amount of soft tissue damage created by inserting and removing resection guide 10. However, it is foreseeable that any incisions can be stretched utilizing retractors or the like or resected portion 4 can be further cut into smaller pieces in situ. Upon removal of resected portion 4, the now resected head 3 remains in the acetabulum of the patient. Thereafter, head 3 can be resected or morsalized to allow for its removal through the incision. This can be done in any fashion known to one of ordinary skill in the art.

It is contemplated that in other embodiments of the present invention, a device like alignment handle 52 or extraction tool 90 can be formed integral with resection guide 10. In these embodiments, extraction tool 90 would be operable for both insertion/alignment and removal of resection guide 10. It should be noted that an extraction tool of this type would need to be configured so as to allow for resection of the bone while being coupled with a resection guide. Furthermore, an extraction tool for use in these embodiments of the present invention would also need to allow for the connection of resection guide 10 to the bone. In certain of these embodiments, the extraction tool could be configured to allow for a screw to be inserted into a hole in resection guide 10 that is located away from the connection between the extraction tool and the guide. However, it is also contemplated that the extraction tool can be formed to include a cannula-like tube that a screw can be inserted through. In this embodiment, the screw would engage a surface, not unlike in the preferred embodiment shown in the Figures, and fixably attach resection guide 10 and extraction tool 90 to the bone.

Another aspect of the present invention is a method for resecting and removing the neck portion of a femur. The method according to this aspect of the invention includes the step of providing a femoral neck resection guide 10 as discussed above. The femoral neck resection guide 10 provided can be in accordance with any of the various embodiments discussed above. Resection guide 10 is then connected to the portion of the femoral neck which is to be cut. It is contemplated that resection guide 10 can be configured for and attached to other bones in accordance with the present invention. However, in a preferred embodiment as discussed in this description of a preferred method in accordance with the present invention, the bone to be resected is the neck portion 2 of femur 1. As discussed above, the connection of resection guide 10 to neck portion 2 can be accomplished in multiple fashions (i.e.—with screws, pins, nails, etc. . . . ). In a preferred embodiment, resection guide 10 is connected to neck portion 2 by a self tapping screw 70.

In the preferred method of use, a surgeon attaches alignment guide 50 to resection guide 10. The surgeon then utilizes alignment guide 50 to insert resection guide 10 into and through a previously created incision in the tissue of a patient. It is noted that this previously created incision can be of any size in any portion of the body. For purposes of discussing a preferred method according to an aspect of the invention, the incision lies in the hip region of a patient and is of a generally small size of approximately 4-6 centimeters (i.e.—minimally invasive). Once resection guide 10 is inserted into the incision, it is brought into contact with neck portion 2 of femur 1. As mentioned above, it is contemplated that alignment guide 50 can be used in conjunction with a navigation tracker mount 68, which provides an electronic mode of navigating resection guide 10 into place. Alternatively, as is also mentioned above, guide 10 can be oriented using guide 50 by aligning portion 52 with the mechanical axis of the femur. Once resection guide 10 is properly positioned, screw 70 is inserted into the incision and into contact with resection guide 10 at aperture 18. The surgeon then threads or advances screw 70 into the bone material of neck portion 2, utilizing any tool useful in performing the function (e.g. a screwdriver or drill). Once resection guide 10 is properly attached to neck portion 2, alignment guide 50 can removed therefrom.

With resection guide 10 in place, the surgeon may now resect the bone to create a resected portion 4. In a preferred embodiment, a surgeon utilizes an oscillating saw blade 80 make to cuts through the bone that correspond to cutting surfaces 14 and 16, respectively. It is contemplated that other cutting devices, such as a reciprocating saw, can also be utilized. As mentioned above, saw blade 80 must be manipulated in a manner to completely resect the bone and create resected portion 4. This requires a surgeon to angle saw blade 80 around bridges 24 and 30 extending between slots 14 and 16. Upon completion of the cuts and creation of cut portion 4, saw blade 80 is removed from the incision.

At this point in the surgical procedure, cut portion 4 is separated from the main portion of femur 1 and femoral head 3 (best shown in FIG. 13). However, resection guide 10 is still connected to resected portion 4, the result of opposing cuts being made on the bone. The next step relates to removing the resection guide 10 and resected portion 4 together. While there are many devices that can be used to remove resection guide 10 from the body, a preferred method in accordance with the present invention uses an extraction tool 90. In use, a surgeon inserts extraction tool 90 into the incision and moves coupling 96 adjacent to resection guide 10. The surgeon can grasp and guide extraction tool 90 by holding handle 92. The surgeon then connects male portions 98 located on coupling 96 with grooves 34 and 38 located on resection guide 10, by rotating extraction tool 90 to lock the two instruments together. Now, any movement imparted upon extraction tool 90 will likewise be imparted on resection guide 10. The surgeon then simply removes resection guide 10, along with resected portion 4 of femur 1, through the incision. Thereafter, femoral head 3 can be resected in situ, using known methods, or removed through the incision, if the incision size permits. The surgeon may now perform the remaining steps in the surgery to be performed (e.g.—total hip replacement surgery).

Another embodiment apparatus for use in resecting the femoral neck is depicted in FIGS. 14-19. More particularly, such figures illustrate a second embodiment femoral neck resection assembly 100, which includes a femoral neck resection guide component 110, a bushing component 140 and a fastener element component 170. Although clearly a separate embodiment from that which is described above, common or similar elements between the embodiments, and variations thereof, are denoted with like reference numerals. However, in the second embodiment depicted in FIGS. 14-19, such elements are set forth within the 100-series of numbers. For instance, FIGS. 1-13 depict a first embodiment femoral neck resection guide 10, while FIGS. 14-19 depict a similar second embodiment femoral neck resection guide 110. The second embodiment will be discussed more fully below.

Figure 14:
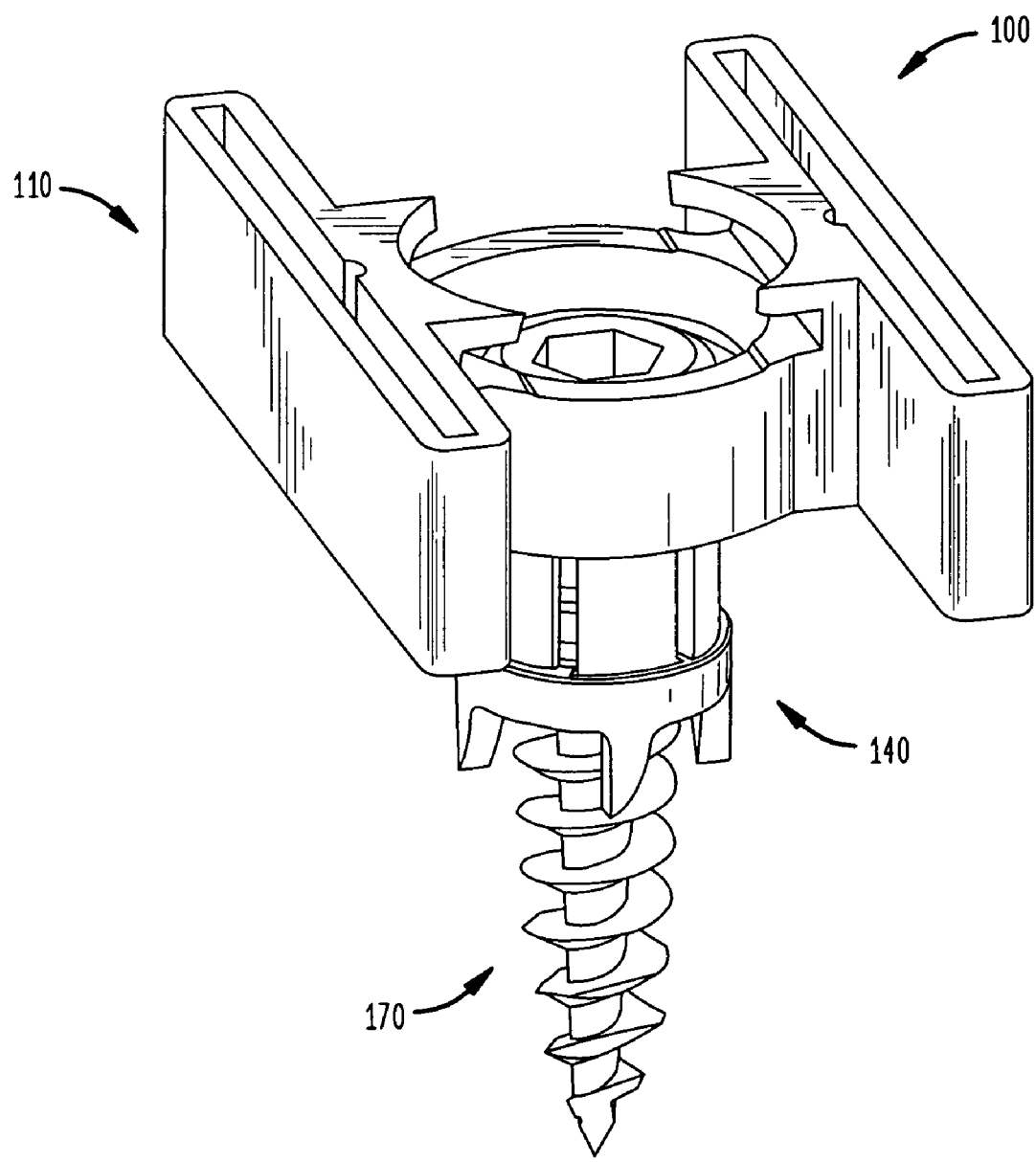
FIG. 14 is a top perspective view of another femoral neck resection guide assembly according to an additional embodiment of the present invention.
Figure 15:
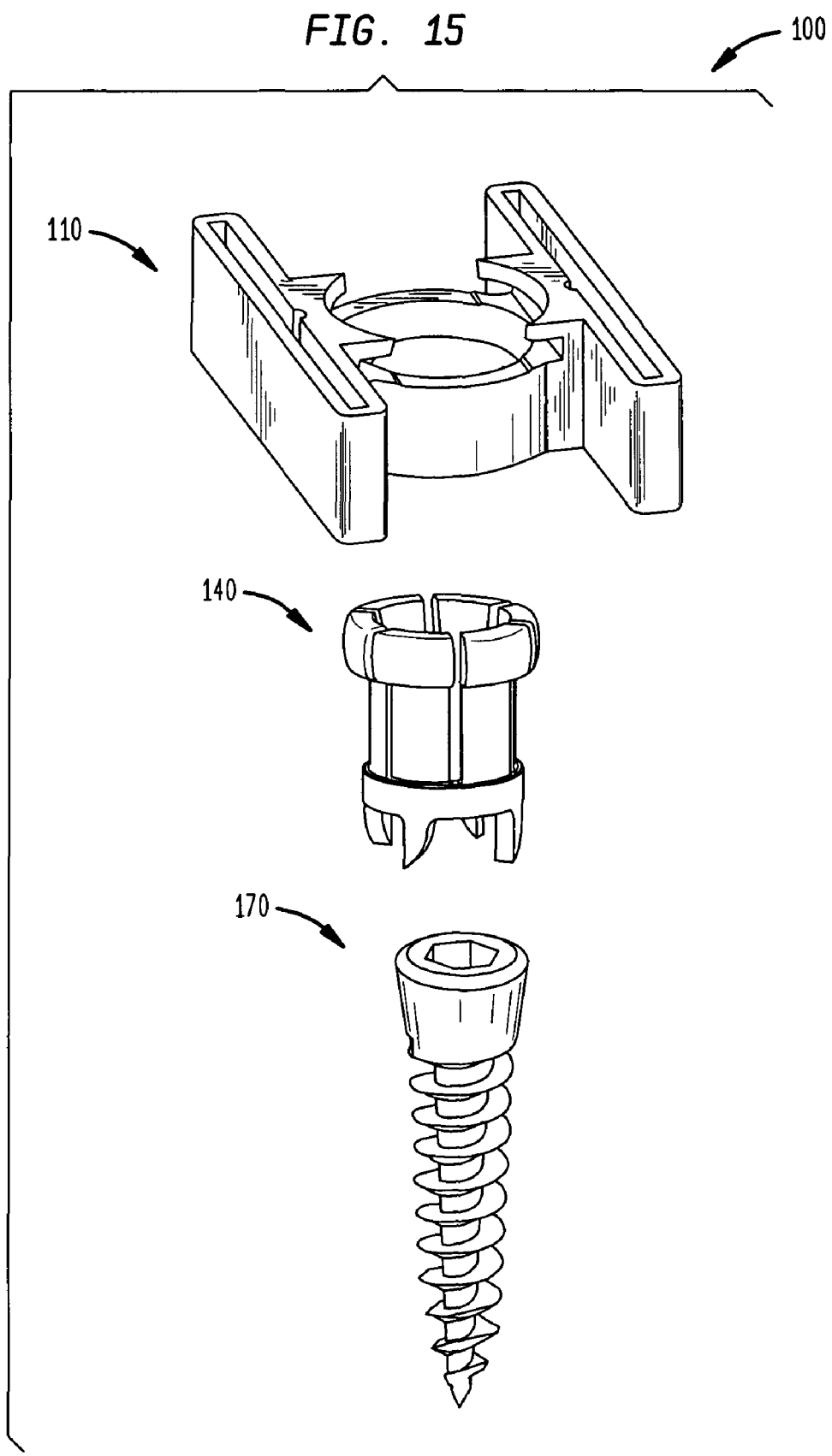
FIG. 15 is an explode view of the femoral neck resection guide assembly shown in FIG. 14.

FIGS. 14 and 15 depict a fully assembled and disassembled femoral neck resection assembly 100, respectively. As is briefly mentioned above, assembly 100 includes a resection guide 110, a bushing 140 and a fastener element or screw 170. As is more clearly shown in FIG. 16, resection guide 110 includes a top surface 106 and a bottom surface 108, with bottom surface 108 ultimately being the surface disposed towards or adjacent the bone surface of neck portion 2 of femur 1. This is not unlike that of the above-discussed resection guide 10. Resection guide 110 also preferably includes a body 112, first and second cutting slots 114, 116 for guiding a cutting tool or the like, and aperture 118 for facilitating connection to neck portion 2. Body 112 connects with first and second cutting slots 114, 116 on either side, and preferably includes aperture 118 formed through it center. As is the case with the first embodiment resection guide 10, first and second cutting slots 114, 116 of guide 110 are preferably spaced apart so that substantially all of femoral neck 2 may be resected. However, once again, it is contemplated that guide 110 may ultimately prove useful and be modified in order to allow for resection of any portion of femoral neck 2, or even other portions of the body. In this regard, it is noted that all applicable variations of the first embodiment resection guide 10 also apply to the second embodiment guide 110.

Body 112 is generally of a cylindrical shape, but can clearly be any shape and/or size, and can be configured to include one or more apertures at any location for use in attaching guide 110 to bone material. In addition, any number of cutting surfaces/slots may be connected with body 112 for facilitating the cutting of a bone. For example, in certain embodiments, body 112 could be square shaped with two apertures and three cutting surfaces attached thereto. This is merely one of many possibilities. However, it is once again worth noting that rounded surfaces of guide 110 help prevent soft tissue damage from occurring during insertion and removal of the guide into and out of the body. This is especially important considering the very small incisions synonymous with MIS procedures. In addition, it is also worth reiterating that cutting slots 114 and 116 may be configured so as to detachably connect with body 112. This may further aid in the insertion and removal of guide 110, as assembly/disassembly in situ could allow for smaller pieces to be passed through the small incision.

Figure 16:
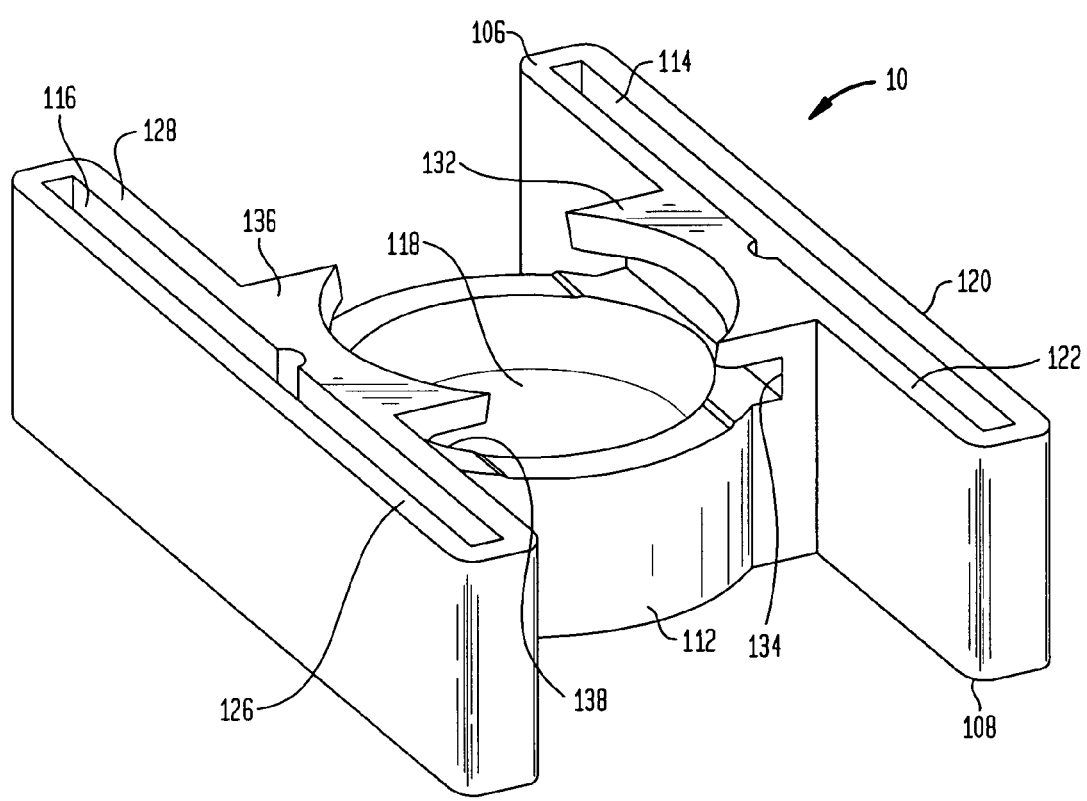
FIG. 16 is a top perspective view of a guide portion of the femoral neck resection guide assembly shown in FIG. 14.

As is also best shown in FIG. 16, first cutting slot 114 is preferably formed by an exterior wall 120 and an interior wall 122, and second cutting slot 116 is preferably formed by an exterior wall 126 and an interior wall 128. However, unlike that shown with regard to guide 10, the exterior and interior walls of slots 114 and 116 are connected together on their respective ends to form a closed cutting slot. Although this is different than the open ended cutting slots described above, it is noted that this is merely another mode of forming a slot, and the open ended mode may also be employed in this second embodiment. Preferably, closed slots 114 and 116 are sized and configured to allow a standard cutting blade or the like to be manipulated therein. This may include the angling and translation of such a cutting instrument, along with other needed movements. It is noted that the closed nature of the slots may aid in the inadvertent slipping of such a cutting instrument, which may, in turn, prevent soft tissue or other bodily damage.

In addition, as is the case in the first embodiment guide 10, guide 110 includes ledges 132 and 136 for use during extraction/removal of the guide. Specifically, ledge 132 is formed at or near the connection between first cutting slot 114 and body 112, and ledge 136 is formed at or near the connection between second cutting slot 116 and body 112. Ledge 132 preferably hangs over body 112 to form a groove 134 and ledge 136 preferably hangs over body 112 to form a groove 138. Ledges 132, 136 and grooves 134, 138 are typically utilized in a similar fashion as the ledges and grooves of guide 10, as is discussed more fully above. Namely, such elements preferably aid in the extraction/removal of guide 110 subsequent to the resection of femoral neck 2.

Figure 17:
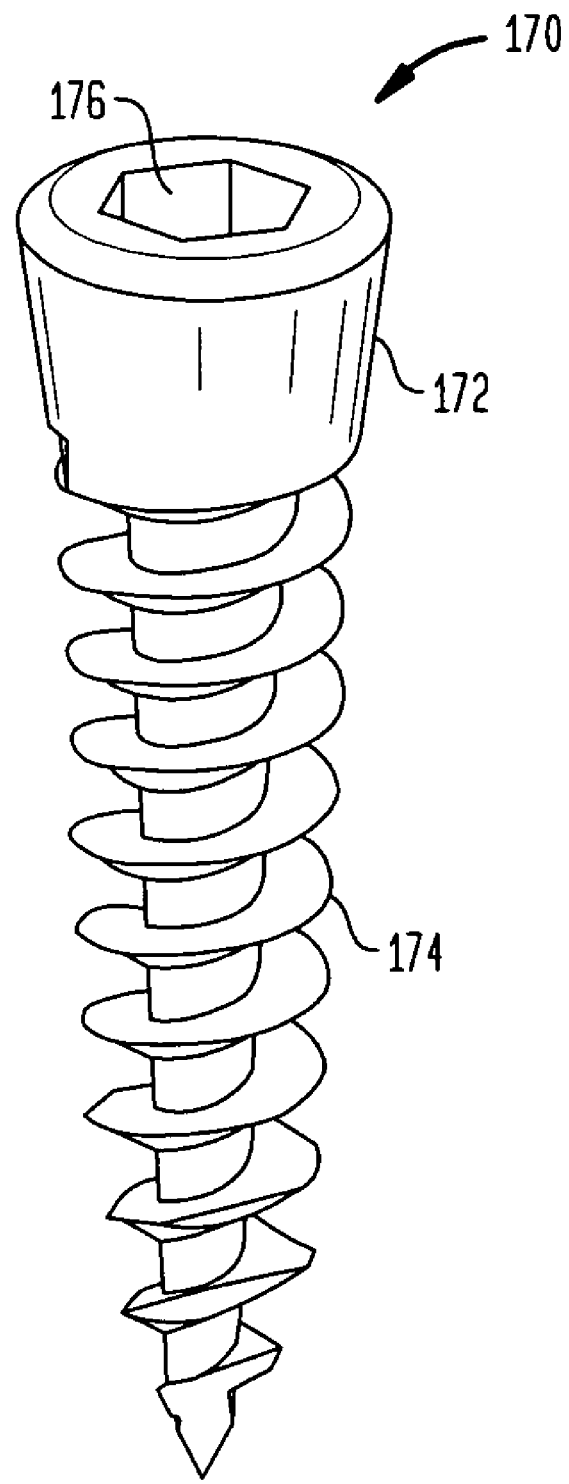
FIG. 17 is a top perspective view of a fastener element of the femoral neck resection guide assembly shown in FIG. 14.

FIG. 17 depicts a fastener element 170 for use in attaching/connecting or otherwise fixing resection guide 110 to the femoral neck or other bone. Essentially, element 170 is a bone screw having a tapered head 172, a threaded portion 174 integrally formed with head 172, and a hexagonal depression 176 formed within head 172 for coupling with a driving tool, such as a screw driver. Such bone screws are well known in the art and may take on other designs, as would be clear to those of ordinary skill in the art. As is shown in FIG. 17, screw 170 is a self tapping bone screw which does not require drilling of the bone prior to its insertion. However, it is contemplated that other, non-self tapping bone screws may be employed. It is noted that screw 170, and in particular the tapered nature of head 172, is sized and configured for cooperation with both guide 110 and bushing 140, as will be discussed more fully below in connection with the description of the bushing and the method of utilizing assembly 100.

Figure 18:
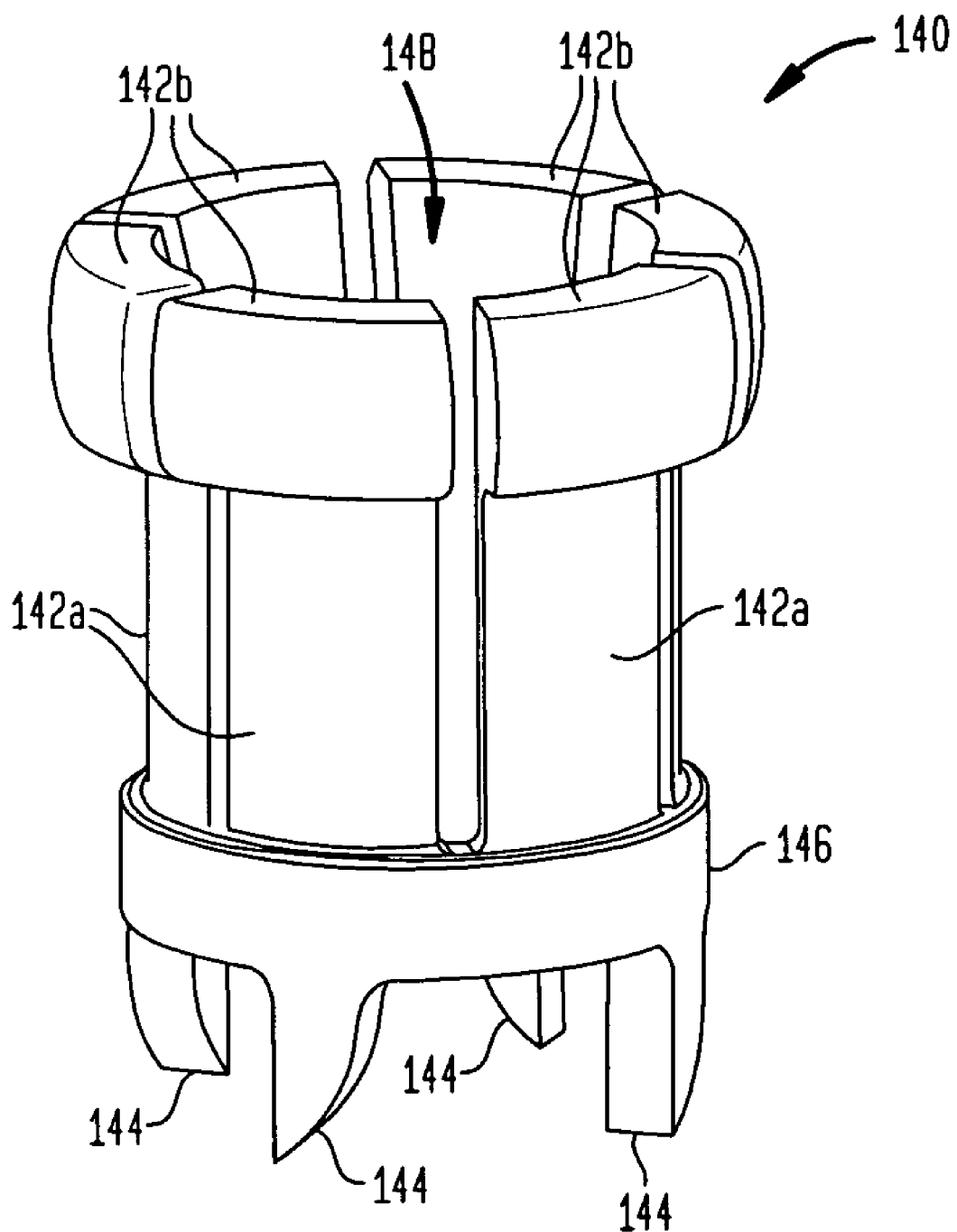
FIG. 18 is a top perspective view of a bushing of the femoral neck resection guide assembly shown in FIG. 14.
Figure 19:
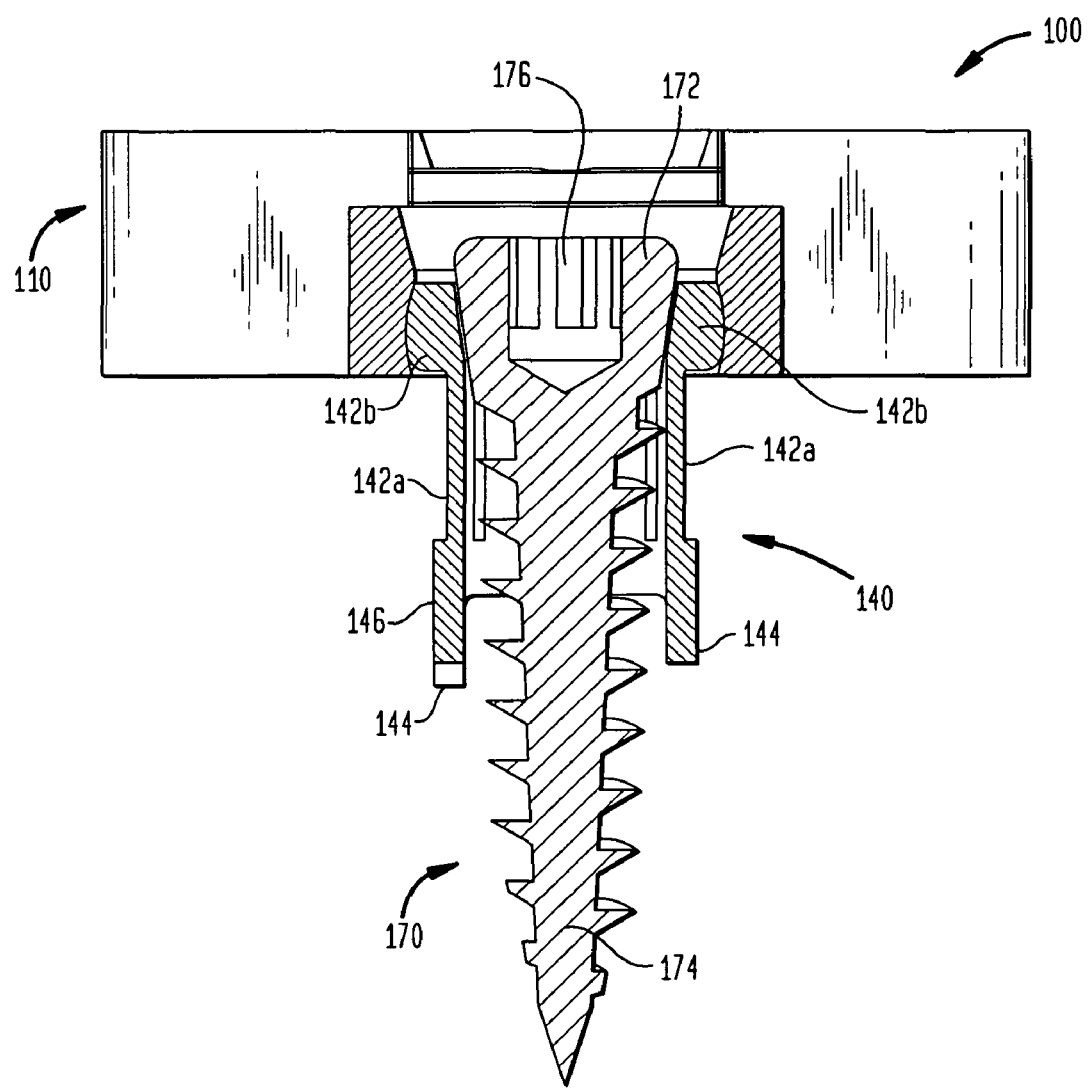
FIG. 19 is a cross sectional view of the cooperation between the guide portion, bushing and fastener element, as shown in FIG. 14.

Bushing 140 is best shown in FIG. 18. This component is meant to cooperate with both guide 110 and screw 170. As is shown in the figure, bushing 140 preferably includes a plurality of radial fingers 142 and a plurality of spikes 144, both connected to a central solid circular portion 146. Although specifically shown in the figures as including six fingers 142 and four spikes 144, it is noted that a bushing in accordance with the present invention may include any number of such elements. For example, it is envisioned to provide bushing 140 with eight fingers 142 and two spikes 144. Each finger 142 further includes a first section 142a and a stepped second section 142b. Finally, bushing 140 defines a hole or aperture 148 having a tapered configuration and being sized and configured to receive a bone screw or the like, e.g.—screw 170. The plurality of first sections 142a preferably make up a circular intermediate portion of bushing 140, while the second sections 142b and body 146 preferably make up top and bottom circular portions, respectively. The intermediate section is preferably narrower than the top and bottom sections, although this does not necessarily need to be the case. In addition, second sections 142b are not only shaped so as to create a top circular portion of bushing 140, but also to have a relatively convex surface, which allows for a particularly useful mating connection with a generally concaved surface of aperture 118 of guide 110. This is best shown in the cross sectional view of FIG. 19.

In the fully constructed assembly 100 (best shown in FIG. 14), bushing 140 is snapped into place within resection guide 110. More particularly, second sections 142b of fingers 142 preferably create a top section with a diameter that allows a snug fit with aperture 118 of resection guide 110. The flexibility created by fingers 142 may allow for easier insertion in this assembly process, and the preferable resilient nature of such fingers also may allow for second sections 142b to snap back after being depressed during insertion. In addition, the convex nature of the surfaces of second sections 142b and the concave nature of the surface of aperture 118 preferably allows for polyaxial rotation of guide 110 with respect to bushing 140, prior to full insertion of screw 70 through hole 148. In other words, prior to fully seating screw 170, resection guide 110 is preferably capable of rotation with respect to bushing 140 about the standard X, Y and Z axis (e.g.—right hand rule), where the X axis is preferably aligned with the axis along the femoral neck. This allows the proper resection level, resection angle and version of the guide to be set. More particularly, the resection level relates to translation along the X axis, the resection angle relates to rotation about the Z axis, and the version relates to rotation about the Y axis, and assembly 100 allows for each to be properly set. The above-discussed cooperation between guide 110 and bushing 140 is not unlike the cooperation depicted between the screws and plates taught in U.S. Pat. No. 5,954,722, the disclosure of which is hereby incorporated by reference herein.

Spikes 144 of bushing 140 are preferably designed so as to prevent any translational and/or rotational movement of bushing 140 once seated in the bone. This allows for rotation of guide 110 to be set without the worry of bushing 140 also moving, and also creates small surfaces that contact the bone as opposed to the entire bottom surface 108 of guide 110. The spikes are preferably seated in the bone upon an initial insertion of screw 170. However, it is contemplated to simply push spikes 144 into the bone of femoral neck 2 prior to any engagement of screw 170 with the other components of assembly 100. Once guide 110 is situated in the correct position, full insertion of screw 170 will cause its tapered head 172 to mate with the like tapered hole 148 of bushing 140. Ultimately, this will preferably result in fingers 142 being pushed radially outward, thereby locking the guide 110 with respect to bushing 140.

Although the basic operation of assembly 100 of the second embodiment is set forth in the preceding paragraphs, a detailed discussion of use of assembly 100 during a surgical procedure is warranted. In a surgical use, such as a hip arthroplasty, the surgeon or other medical professional would first make an incision in accordance with the type of hip surgical procedure being performed (e.g.—an MIS procedure). Thereafter, resection guide 110 and bushing 140 are preferably assembled together. However, such may be done prior to surgery, for example, just after manufacture and prior to packaging of assembly 100. A surgeon then preferably attaches guide 110, with bushing 140 attached thereto, to a suitable insertion guide (not shown). It is contemplated that the above-described insertion guide 50 could be utilized for the insertion of guide 110 and bushing 140. It is especially preferably that navigation tracker mount 68 of guide 50 be utilized in conjunction with a navigation tracker (not shown). This will be important in aiding in properly positioning guide 110 for resection of femoral head 2.

Once guide 110 is attached to a suitable insertion guide, such is preferably placed into the incision and towards femoral neck 2 of femur 1. Depending upon where the incision is created, this may involve movement in one direction or another. In addition, if guide 110 is designed to include modular components, as is clearly contemplated by the present invention, such would preferably be constructed in situ prior to significant movement towards the femoral neck, i.e.—closer to the surface of the skin. Once guide 110 and bushing 140 are adjacent femoral neck 2, the insertion guide may be utilized to at least partially push spikes 144 of bushing 140 into the bone. This prevents any further movement of bushing 140, but the rotational cooperation between such and guide 110 allows for further positioning of the latter. Alternatively, once guide 110 and bushing 140 are adjacent femoral neck 2, screw 170 may be inserted into hole 148 of the bushing. This may be accomplished by passing screw 170 through, for example, an opening in a portion of the insertion guide, similar to central opening 66 in platform 56 of guide 50 of the first embodiment. Thereafter, initial insertion of screw 170 into bone could be designed so as to push spikes 144 of bushing 140 into the bone. Regardless of which fashion is undertaken, the surgeon now preferably has a guide 110 which he/she can rotate with respect to a fixed bushing 140 and with respect to femoral neck 2.

With regard to positioning guide 110, it is first noted that a surgeon is typically interested in setting the correct resection level, resection angle and version, as is discussed above. These typically relate to movement and/or rotation of guide 110 about the standard X, Y and Z axes (also discussed above). A navigation tracker connected with, for example, a navigation tracker 68 of guide 50, or some other suitable guide, may aid in achieving the proper positioning of the guide. Namely, a tracker or other positioning aid preferably allows for any movement of the insertion guide (such as rotational movement), and thusly guide 110, to be tracked on a computer screen or other visual device. Such navigation trackers and methods are well known in the art, and some examples are described in the above-mentioned and incorporated '343 and '415 patents. In addition, such navigation devices and programs may include markers for properly determining and setting the correct positioning of guide 110. Again, the cooperation between guide 110 and bushing 140 allows for the polyaxial rotation needed to set the guide in position.

Once the proper position of resection guide 110 is achieved, either screw 170 can then be inserted through hole 148 and fully into bone, or a previously partially implanted screw 170 can be fully inserted into the bone. Whatever the case, the tapered configuration of both head 172 of screw 170 and hole 148 of bushing 140 preferably causes fingers 142 to expand upon insertion of the screw. Essentially, upon full insertion of screw 170, fingers 142 are forced outwardly and into direct contact with aperture 118 of guide 110. This creates a snug fit which may totally prevent further rotation of guide 110 with respect to bushing 140, and the full insertion of screw 170 into the bone will create a static fixation with the femoral neck. Thus, the guide will now be fixed in a position suitable for resecting femoral neck 2. It is noted that any insertion guide being employed may be held in place during the insertion of screw 170, in order to hold guide 110 in the desired position. This may or may not involve affixing the insertion guide to an exterior support.

Once guide 110 is fixed with respect to femoral neck 2, the resection and ultimate extraction of at least a portion of femoral neck 2 may be carried out in a similar fashion as discussed above in relation to the first embodiment. For example, a suitable cutting device (like saw blade 80) may be guided by slots 114 and 116, and a suitable extraction device (like extraction tool 90) may be utilized to remove guide 110, bushing 140 and the resected portion. Of course all variations in the method, as discussed in relation to the first embodiment, also apply to the method utilizing assembly 100.

Finally, it is noted that other embodiments of the present invention are contemplated. For example, an assembly is envisioned in which the cooperation between a guide and a bushing (like guide 110 and bushing 140) not only allows for polyaxial rotation, but also for translation or other types of movements. Although not shown in the figures, a person of ordinary skill in the art would readily recognize the necessary modifications needed for producing such an assembly. The operation of this type of assembly may allow a surgeon to further position a cutting guide without the need for pin pointing a specific initial insertion area for a bushing. In other words, bushing may simply be placed on any portion of the bone, and the guide may be translated into position, as well as being finely rotated to achieve proper positioning. Of course, such an additional embodiment could employ and and all of the aforementioned features of any of the other embodiments discussed herein. In addition, the differing features of this embodiment may likewise be applied to any of the other discussed embodiments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of removing a neck of a femur comprising:
    providing a femoral neck resection guide assembly including a guide, a bushing and a fastener element, the bushing having a bottom surface;
    aligning at least the guide and bushing with respect to a portion of the femoral neck;
    seating at least a portion of the bushing in the portion of the femoral neck;
    positioning the guide with respect to the bushing;
    locking the guide with respect to the bushing and the femoral neck by inserting the fastener element in the bushing and penetrating into the portion of the femoral neck, the fastener element extending below the bottom surface of the bushing; and
    resecting the portion of the femoral neck with a cutting tool guided by the guide while the guide remains attached to the portion of the femoral neck.

2. The method of claim 1, further comprising the step of removing the femoral neck resection guide assembly.

3. The method of claim 2, wherein the removal step further includes removing the portion of the femoral neck attached to the assembly.

4. The method of claim 1, wherein the aligning step further includes attaching at least the guide and bushing to an insertion instrument.

5. The method of claim 4, wherein the insertion instrument is capable of cooperating with a navigation tracker for tracking the position of the guide.

6. The method of claim 1, wherein the seating step includes engaging at least one spike disposed on the bushing with the portion of the femoral neck.

7. The method of claim 1, wherein the positioning step includes polyaxially rotating the guide with respect to the bushing.

8. The method of claim 1, wherein the locking step includes engaging the fastener element with the bushing to expand at least a portion of the bushing to prevent rotation of the guide with respect to the bushing.

9. The method of claim 8, wherein the fastener element is a screw having a tapered head for engagement with expandable fingers of the bushing.

10. The method of claim 1, wherein the resecting step includes resecting substantially all of the femoral neck.

11. The method of claim 1, wherein the resecting step includes operating a cutting tool.

12. The method of claim 11, wherein the cutting tool is a saw guided by slots disposed on the guide.

13. The method of claim 1, further including the step of assembling the guide with the bushing.

14. The method of claim 1, further comprising the step of removing the resected portion of the femoral neck attached to the assembly.

15. A method of removing a neck of a femur comprising:
    providing a femoral neck resection guide assembly including a guide, a bushing and a fastener element;
    attaching an insertion instrument to the guide and the bushing;
    seating at least a portion of the bushing in a portion of the femoral neck;
    positioning the guide with respect to the bushing;
    placing the fastener element through the bushing and the guide and threading the fastener element into the portion of the femoral neck to lock the guide with respect to the bushing; and
    resecting the portion of the femoral neck with a cutting tool guided by the guide while the guide remains attached to the portion of the femoral neck.

16. The method of claim 15, wherein the seating step includes engaging at least one spike disposed on the bushing with the portion of the femoral neck.

17. The method of claim 15, wherein the positioning step includes polyaxially rotating the guide with respect to the bushing.

18. The method of claim 15, wherein the locking step includes engaging the fastener element with the bushing to expand at least a portion of the bushing to prevent movement of the guide with respect to the bushing.

19. The method of claim 18, wherein the fastener element is a screw having a tapered head for engagement with expandable fingers of the bushing.

20. The method of claim 15, further including the step of assembling the guide with the bushing.

21. The method of claim 15, wherein the resecting step includes operating a cutting tool.

22. The method of claim 14, wherein the removal step includes reattaching the insertion instrument.

23. The method of claim 14, wherein the insertion instrument is capable of cooperating with a navigation tracker for tacking the position of the guide.

24. A method of removing a neck of a femur comprising:
providing a femoral neck resection guide assembly including a guide, a bushing and a fastener element;
assembling the guide with the bushing;
attaching an insertion instrument to the guide and the bushing;
engaging at least one spike of the bushing with a portion of the femoral neck;
positioning the guide with respect to the bushing;
placing the fastener element through the bushing and the guide and threading the fastener element into the portion of the femoral neck so that a head of the fastener expands expandable fingers of the bushing to lock the guide with respect to the bushing; and
resecting the portion of the femoral neck with a cutting tool guided by the guide.

25. The method of claim 24, wherein the bushing includes six expandable fingers and four spikes.

26. The method of claim 25, wherein the head of the fastener is tapered.

27. The method of claim 24, wherein the step of assembling the guide with the bushing includes placing the bushing in an aperture formed in the guide.

28. The method of claim 24, wherein the resecting step includes operating a cutting tool.

29. The method of claim 28, wherein the cutting tool is a saw guided by slots of the guide.

30. The method of claim 24, further comprising the step of removing the portion of the femoral neck attached to the assembly.

31. The method of claim 30, wherein the removal step includes reattaching the insertion instrument.

32. The method of claim 24, wherein the insertion instrument is capable of cooperating with a navigation tracker for tacking the position of the guide.

* * * * *